Feb. 2, 1971 G. MERRILL Plant Pat. 3,023
PEACH TREE
Filed Jan. 29, 1969
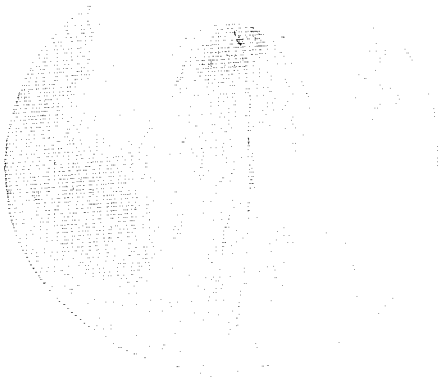
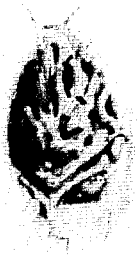
GRANT MERRILL
INVENTOR
Virgil L. Gerard
ATTORNEY

United States Patent Office

Plant Pat. 3,023
Patented Feb. 2, 1971

3,023
PEACH TREE

Grant Merrill, 416 N. Anderson Road, Exeter, Calif. 93221

Filed Jan. 29, 1969, Ser. No. 795,127
Int. Cl. A01h *5/03*
U.S. Cl. Plt.—43 1 Claim

The present invention relates to a peach tree and more particularly to a new and distinct variety thereof broadly characterized by a vigorous and productive tree, and by large size fruit, half or more of which is highly colored with red on the skin surface, and which holds its firmness on the tree so that fewer pickings are necessary and the fruit can be handled by machine with less bruising than other peaches ripening at this season. In addition, the texture and color of the flesh, and its complete freedom from the stone, make the fruit of this variety of peach good from commercial freezing.

The instant variety, July Lady (28–28E), most nearly resembles the Angelus (U.S. Plant Pat. No. 1,966) but differs therefrom and is an improvement thereon in that it ripens a few days earlier, shows more red on the skin, and is firmer so that fewer pickings are necessary and machine handling causes less bruising.

I originated the present variety on a farm near Red Bluff, Tehama County, Calif., by crossing J. H. Hale (unpatented) with Merrill Gem (U.S. Plant Pat. No. 868), planting the seeds thereof, and then taking the seeds from the fruit growing on the resulting tree and growing them. One of the resulting seedlings was asexually propagated onto a mature tree on my farm near Exeter, Tulare County, Calif., and the resulting tree and fruit were exactly the same as those on the original tree at Red Bluff and proved exceptionally successful in the ecological conditions of the San Joaquin Valley of California.

The accompanying drawing is an oil painting of a characteristic fruit of the subject variety including a showing of the fruit divided on its suture plane to reveal flesh coloration and stone characteristics.

Referring more specifically to the pomological characteristics of this new and distinct variety of peach tree, the following has been observed under the ecological conditions prevailing at Exeter, Tulare County, Calif., and is an outline description thereof. All major color plate identifications are by reference to Maerz and Paul Dictionary of Color, 1st ed.

TREE

Production characteristics: medium size tree, medium spread productive, regular bearer.

Trunk: medium in dimensions; gray color; bark, medium shaggy.

Branches: medium in dimensions; grey and shaggy on older branches; smoother and brown on younger branches; lenticels, medium in size and quantity.

Leaves: medium in size, length 4 to 7½ inches, width, ¾ to 1¾ inches; lanceolate in shape; tip, accuminate; medium thick; color, upper surface medium dark green, under surface, light green; veins on underside, yellow green; class (Meader & Blake: Proceeding of the American Society for Horticultural Science, vol. 37, p. 204) two; width-length ratio 4½ to 6:1; margin, glandular crenate; petiole, medium size, ⅜ to ⅝ inch long; glands, reniform, number 1 to 4, alternate, medium size, generally yellow to brown in color, mostly on petiole, few on base of leaves.

FLOWERS

Buds: medium size, pubescent, plump, free.

Flowers: small in size, early (about with July Elberta, U.S. Plant Pat. 15), pinkish salmon color, pollen abundant.

FRUIT

Maturity: (when described): firm ripe, July 31, 1968; season of ripening a few days to a week earlier than Elberta (unpatented).

Size: large, variable in shape, generally globose; axial diameter 2⅝ to 3⅛ inches; transverse in suture plane 2½ to 3¼ inches; right angle to suture plane 2⅜ to 3¼ inches.

Suture: slight ridge and shallow groove in most.

Dorsal side: rounded.

Cavity: flaring, elongated in suture plane, and showing on both sides; depth ⅜ to ⅝ inch; markings, undercolor yellow with red blush when exposed to the sun.

Apex: retuse; pistil point, apical, short, almost nonexistent in some, up to ⅛ inch in some.

Stem: short.

Skin: medium in thickness, medium tender, sweet, tencious to flesh; pubescence, scant; color, light yellow 9L2 to medium yellow, 9J9 to dark yellow 9H12 undercolor, with red blush from 2F11 to 5L2 to dark red 7C6.

Flesh: generally light yellow 9G2 to medium yellow 9G6, with red near stone and sometimes in specks throughout the flesh, lightest red 3L9 to darker red 7A6; amygdalin, moderate; juice, moderate; texture, meaty; fibers, short, fine and few; ripening evenly; flavor, subacid and mild; firm throughout; aroma distinct; eating quality good.

Stone: completely free from the flesh; size, medium to small; length, 1⅛ to 1⅜ inches; width 13/16 to 1⅛ inches; thickness, ⅝ to ¾ inch; generally obovate; base, straight to oblique; helium, oval; apex, accuminate; sides, equal and unequal; surface, furrowed and pitted throughout; some elongated; ventral edge, raised with many fine grooves; pits, generally circular, some oblong; dorsal edge, with deep grooves on each side from base usually ¾ way to apex; color dark brown when fresh, brown to tan when dried; tendency to split, slight.

Use: general fresh market, freezing.

Eating quality: good.

Shipping quality: excellent.

Although the new variety of peach tree possesses the described characteristics under the ecological conditions prevailing in Exeter, Tulare County, Calif., having been first observed near Red Bluff, Tehama County, Calif., it is to be understood that variations of the usual magnitude in characteristics incident to the growing conditions, fertilization, pruning and pest control is to be expected.

Having thus described and illustrated my new variety of peach tree, what is claimed is:

1. A new and distinct variety of peach substantially as illustrated and described and which is characterized by a vigorous and productive tree, bearing large size fruit with a skin color which is red over half or more of the surface; which fruit is sufficiently firm to require fewer pickings, and permit machine handling, with less bruising than other peaches of like season, has flesh which is officiencyl free from the stone, and is clear enough in flesh color to make a good freezing peach; and by its resemblance to Angelus (U.S. Plant Pat. 1,966) from which it is distinguished primarily by its greater firmness and more extensive red coloring on the skin.

No references cited.

ROBERT E. BAGWILL, Primary Examiner